United States Patent
Pasquier et al.

(10) Patent No.: US 7,294,151 B2
(45) Date of Patent: Nov. 13, 2007

(54) MEANS AND METHOD FOR DYEING KERATIN FIBRES

(75) Inventors: Cécile Pasquier, Marly (CH); Caroline Kiener, Marly (CH); Hans-Juergen Braun, Ueberstorf (CH)

(73) Assignee: Wella AG, Darmstadt (DE)

(*) Notice: Subject to any disclaimer, the term of this patent is extended or adjusted under 35 U.S.C. 154(b) by 341 days.

(21) Appl. No.: 10/529,979

(22) PCT Filed: Jan. 30, 2004

(86) PCT No.: PCT/EP2004/000815

§ 371 (c)(1),
(2), (4) Date: Mar. 24, 2005

(87) PCT Pub. No.: WO2004/078151

PCT Pub. Date: Sep. 16, 2004

(65) Prior Publication Data

US 2006/0070190 A1    Apr. 6, 2006

(30) Foreign Application Priority Data

Mar. 5, 2003 (DE) ................. 103 09 521

(51) Int. Cl.
*A61K 7/13* (2006.01)
(52) U.S. Cl. ............. 8/405; 8/406; 8/408; 8/409; 8/573; 8/575; 8/576; 548/146
(58) Field of Classification Search ............. 8/405, 8/406, 408, 409, 573, 575, 576; 548/146
See application file for complete search history.

(56) References Cited

U.S. PATENT DOCUMENTS 3,634,013 A * 1/1972 Maul et al. ............. 8/409

FOREIGN PATENT DOCUMENTS

| DE | 1 922 400 | 12/1969 |
|----|-----------|---------|
| WO | 02/074267 A1 | 9/2002 |
| WO | 02/074268 A2 | 9/2002 |

OTHER PUBLICATIONS

STIC Search Report dated on Apr. 3, 2007.*
Vorschrift in Research Disclosure, Oct. 1978, pp. 42-44, No. 17434.

* cited by examiner

*Primary Examiner*—Eisa Elhilo
(74) *Attorney, Agent, or Firm*—Michael J. Striker

(57) ABSTRACT

The agent for coloring keratin fibers is based on oxidative dye precursors and contains:
(a) at least one hydrazone derivative of formula (I) or a physiologically compatible salt thereof,
(b) at least one coupler or a physiologically compatible salt thereof, and
(c) a persulfate salt as oxidant. A multicomponent kit for coloring keratin fibers and a method of coloring keratin fibers using the agent are also provided

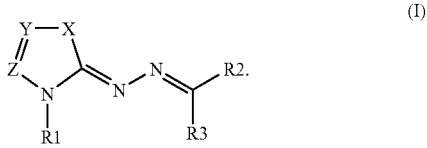

13 Claims, No Drawings

MEANS AND METHOD FOR DYEING KERATIN FIBRES

CROSS-REFERENCE

This is the U.S. National Stage of PCT/EP04/000815, filed on Jan. 30, 2004, in Europe, which, in turn, is based on DE 103 09 521.7, which was filed in Germany on Mar. 5, 2003. The foregoing German Patent Application discloses substantially the same invention as described herein below and provides the basis for a claim of priority of invention for the invention described herein below under 35 U.S.C. 119 (a) to (d).

BACKGROUND OF THE INVENTION

The present invention has for an object an agent for coloring keratin fibers, for example silk, wool or hair and particularly human hair, based on oxidation dye precursors and which contains at least one heterocyclic hydrazone derivative of formula (I) and at least one persulfate salt as oxidant, and furthermore a multicomponent kit and a method for coloring keratin fibers by use of said agent.

SUMMARY OF THE INVENTION

It is an object of the present invention to provide an agent, kit and a method for coloring keratin fibers that satisfies the requirements for colorant systems better than the known conventional colorant systems.

Hair colorants are divided mainly into the group of oxidative colorants or that of tinting agents, depending on the color of the hair to be dyed and on the end result desired. Oxidative colorants are eminently suited for covering large gray areas for which, when the proportion of gray hair is 50%, the oxidative colorants used are usually referred to as oxidative tinting agents, whereas the oxidative colorants used when the proportion of gray hair is greater than 50% or for "brightening" are usually referred to as oxidative dyes Direct dyes are contained mainly in non-oxidative colorants (known as tinting colorants). Some direct dyes, for example nitro dyes, can, because of their small [molecular] size, penetrate into the hair and dye the hair directly, at least in the outer regions. Such tinting agents are very gentle to the hair and as a rule withstand 6 to 8 hair washes, Direct dyes are often also used in oxidative colorants to create certain shades or for color intensification. The colorant systems known to date, however, do not meet the requirements placed on colorants in every respect, particularly in terms of luster and coloration intensity.

Surprisingly, we have now found that certain heterocyclic hydrazone derivatives give with conventional couplers, for example aromatic compounds containing hydroxyl and/or amino groups, in the presence of persulfate salts, intense colorations in the yellow to blue color range. The novel colorants gives particularly brilliant and intense colorations showing very high resistance to perspiration.

According to the present invention the agent for coloring keratin fibers (A), for example wool, silk or hair and particularly human hair, contains a) at least one hydrazone derivative of formula (I) or a physiologically compatible salt thereof:

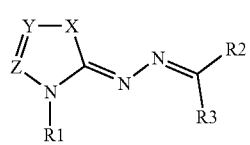

wherein X denotes oxygen, sulfur or N—R4;
Y denotes C—R5 or nitrogen and
Z denotes C—R6 or nitrogen;
provided that the heterocyclic part of the compound of formula (I) contains at the most three heteroatoms;
R1 and R4 can be equal or different and independently of each other stand for a saturated or unsaturated $(C_1-C_{12})$-alkyl group, a $(C_1-C_{12})$-alkyl group substituted with a halogen atom (F, Cl, Br, I), a hydroxy-$(C_1-C_{12})$-alkyl group, an amino-$(C_1-C_{12})$-alkyl group, a $(C_1-C_{12})$-alkyl-sulfonic acid group, a formyl group, a C(O)—$(C_1-C_{12})$-alkyl group, a substituted or unsubstituted C(O)-phenyl group, a C(O)NH—$(C_1-C_{12})$-alkyl group, a C(O)NH-phenyl group, a substituted or unsubstituted phenyl group or a benzyl group;
R2 and R3 can be equal or different and independently of each other denote a saturated or unsaturated $(C_1-C_{12})$-alkyl group;
R5 and R6 can be equal or different and independently of each other stand for hydrogen, a halogen atom (F, Cl, Br, I), a saturated or unsaturated $(C_1-C_{12})$-alkyl group, a $(C_1-C_{12})$-alkyl group substituted with a halogen atom (F, Cl, Br, I), a $(C_1-C_{12})$-hydroxyalkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a C(O)O—$(C_1-C_{12})$-alkyl group, a substituted or unsubstituted C(O)O-phenyl group, a substituted or unsubstituted phenyl group or a naphthyl group;
and when Y and Z denote C—R3 and C—R4, then R5 and R6 together with the remainder of the molecule form a heterocyclic or carbocyclic, saturated or unsaturated, substituted or unsubstituted ring system;
(b) at least one coupler or a physiologically compatible salt thereof, and
(c) a persulfate salt as oxidant.

Preferred are hydrazone derivatives of formula (I) or the physiologically compatible salts thereof wherein X stands for sulfur, Y and Z denote C—R5 and C—R6, and R2 and R3 denote a methyl group, and particularly preferred are the hydrazone derivatives of formula (I) or the physiologically compatible salts thereof wherein X stands for sulfur, R2 and R3 denote a methyl group, R1 denotes a saturated or unsaturated $(C_1-C_{12})$-alkyl group, a hydroxy-$(C_1-C_{12})$-alkyl group, an amino-$(C_1-C_{12})$-alkyl group or a substituted or unsubstituted phenyl group, and R5 and R6 independently of each other denote hydrogen, a saturated or unsaturated $(C_1-C_{12})$-alkyl group, a cyano group, a nitro group, an amino group, a $(C_1-C_{12})$-alkylamino group, a $(C_1-C_{12})$-dialkylamino group, a C(O)O—$(C_1-C_{12})$-alkyl group or a substituted or unsubstituted phenyl group or a naphthyl group, or R5 and R6 together with the remainder of the molecule form a carbocyclic, unsaturated, substituted or unsubstituted ring system.

The following compounds may be mentioned as examples of compounds of formula (I):

3-methyl-2(3H)-thiazolone-(1-methylethylidene)hydrazone,
3,4-dimethyl-2(3H)-thiazolone-(1-methylethylidene)hydrazone,
3-methyl-4-tert.butyl-2(3H)-thiazolone-(1-methylethylidene)hydrazone,
3-methyl-4-phenyl-2(3H)-thiazolone-(1-methylethylidene)hydrazone,
3-methyl-4-(4-tolyl)-2(3H)-thiazolone-(1-methylethylidene)hydrazone,
4-(4-methoxy)phenyl-3-methyl-2(3H)-thiazolone-(1-methylethylidene)hydrazone,
4-(3-hydroxyphenyl)-3-methyl-2(3H)-thiazolone-(1-methylethylidene)hydrazone,
4-(4-ethoxyphenyl)-3-methyl-2(3H)-thiazolone-(1-methylethylidene)hydrazone,
4-(4-bromophenyl)-3-methyl-2(3H)-thiazolone-(1-methylethylidene)hydrazone,
4-(3-bromophenyl)-3-methyl-2(3H)-thiazolone-(1-methylethylidene)hydrazone,
4-(4-chlorophenyl)-3-methyl-2(3H)-thiazolone-(1-methylethylidene)hydrazone,
4-(3-chlorophenyl)-3-methyl-2(3H)-thiazolone-(1-methylethylidene)hydrazone,
3-methyl-4-(4-nitrophenyl)-2(3H)-thiazolone-(1-methylethylidene)hydrazone,
3-methyl-4-(3-nitrophenyl)-2(3H)-thiazolone-(1-methylethylidene)hydrazone,
4-([1,1'-biphenyl]-4-yl)-3-methyl-2(3H)-thiazolone-(1-methylethylidene)hydrazone,
3-methyl-4-(2-naphthalenyl)-2(3H)-thiazolone-(1-methylethylidene)hydrazone,
ethyl 2-[(1-methylethylidene)hydrazono]-2,3-dihydro-3-methyl-4-thiazolecarboxylate,
3,4,5-trimethyl-2(3H)-thiazolone-(1-methylethylidene)hydrazone,
3,4-dimethyl-5-phenyl-2(3H)-thiazolone-(1-methylethylidene)hydrazone,
3,5-dimethyl-4-phenyl-2(3H)-thiazolone-(1-methylethylidene)hydrazone,
3-methyl-4,5-diphenyl-2(3H)-thiazolone-(1-methylethylidene)hydrazone,
5-ethyl-3-methyl-4-phenyl-2(3H)-thiazolone-(1-methylethylidene)hydrazone,
4-(4-bromophenyl)-3-methyl-5-phenyl-2(3H)-thiazolone-(1-methylethylidene)hydrazone,
3-methyl-5-phenyl-4-(4-tolyl)-2(3H)-thiazolone-(1-methylethylidene)hydrazone,
5-(4-chlorophenyl)-4-phenyl-3-methyl-2(3H)-thiazolone-(1-methylethylidene)hydrazone,
5-(4-chlorophenyl)-4-(4-methoxyphenyl)-3-methyl-2(3H)-thiazolone-(1-methylethylidene)hydrazone,
ethyl 2-[(1-methylethylidene)hydrazono]-2,3-dihydro-3,4-dimethyl-4-thiazololecarboxylate,
4-amino-2-[(1-methylethylidene)hydrazono]-2,3-dihydro-3-methyl-5-thiazolecarbonitrile,
3-ethyl-4,5-dimethyl-2(3H)-thiazolone-(1-methylethylidene)hydrazone,
ethyl 2-[(1-methylethylidene)hydrazono]-2,3-dihydro-3-ethyl-4-methylthiazolecarboxylate,
5-methyl-3-(1-methylethyl)-4-phenyl-2(3H)-thiazolone-(1-methylethylidene)hydrazone,
4,5-dimethyl-3-(1-methylethyl)-2(3H)-thiazolone-(1-methylethylidene)hydrazone,
3-(1-methylethyl)-4,5-diphenyl-2(3H)-thiazolone-(1-methylethylidene)hydrazone,
3-(1-methylethyl)-4,5-diphenyl-2(3H)-thiazolone-(1-methylethylidene)hydrazone,
4-methyl-3-propyl-2(3H)-thiazolone-(1-methylethylidene)hydrazone,
4,5-dimethyl-3-propyl-2(3H)-thiazolone-(1-methylethylidene)hydrazone,
4,5-diphenyl-3-propyl-2(3H)-thiazolone-(1-methylethylidene)hydrazone,
3-butyl-4,5-dimethyl-2(3H)-thiazolone-(1-methylethylidene)hydrazone,
3-butyl-4,5-diphenyl-2(3H)-thiazolone-(1-methylethylidene)hydrazone,
4,5-dimethyl-3-(2-methylpropyl)-2(3H)-thiazolone-(1-methylethylidene)hydrazone,
3-(2-methylpropyl)-4,5diphenyl-2(3H)-thiazolone-(1-methylethylidene)hydrazone,
3-hydroxyethyl-2(3H)-thiazolone-(1-methylethylidene)hydrazone,
3-hydroxyethyl-4-methyl-2(3H)-thiazolone-(1-methylethylidene)hydrazone,
3-hydroxyethyl-4,5-methyl-2(3H)-thiazolone-(1-methylethylidene)hydrazone,
3-aminoethyl-2(3H)-thiazolone-(1-methylethylidene)hydrazone,
3-aminoethyl-4-methyl-2(3H)-thiazolone-(1-methylethylidene)hydrazone,
3-aminoethyl-4,5-dimethyl-2(3H)-thiazolone-(1-methylethylidene)hydrazone,
3-allyl-2(3H)-thiazolone-(1-methylethylidene)hydrazone,
3-allyl-4-methyl-2(3H)-thiazolone-(1-methylethylidene)hydrazone,
3-allyl-4-tert.butyl-2(3H)-thiazolone(1-methylethylidene)hydrazone,
3-allyl-4-phenyl-2(3H)-thiazolone-(1-methylethylidene)hydrazone,
3-allyl-4,5-dimethyl-2(3H)-thiazolone-(1-methylethylidene)hydrazone,
3-allyl-4,5-diphenyl-2(3H)-thiazolone-(1-methylethylidene)hydrazone,
3-phenyl-2(3H)-thiazolone-(1-methylethylidene)hydrazone,
3,4-phenyl-2(3H)-thiazolone-(1-methylethylidene)hydrazone,
4-methyl-3-phenyl-2(3H)-thiazolon-(1-methylethylidene)hydrazone,
4-p-biphenylyl-3-phenyl-2(3H)-thiazolone-(1-methylethylidene)hydrazone,
4-(4-methoxy)phenyl-3phenyl-2(3H)-thiazolone-(1-methylethylidene)hydrazone,
4-tert.butyl-3phenyl-2(3H)-thiazolone-(1-methylethylidene)hydrazone,
ethyl 2-[(1-methylethylidene)hydrazono]-2,3-dihydro-3-phenyl-4-thiazoloacetoacetate,
4,5-dimethyl-3-phenyl-2(3H)-thiazolone-(1-methylethylidene)hydrazone,
5-methyl-3,4-diphenyl-2(3H)-thiazolone-(1-methylethylidene)hydrazone,
3,4,5-triphenyl-2(3H)-thiazolone-(1-methylethylidene)hydrazone,
4,5-dimethyl-3-(phenylmethyl)-2(3H)-thiazolone-(1-methylethylidene)hydrazone,
4-phenyl-3-(phenylmethyl)-2(3H)-thiazolone-(1-methylethylidene)hydrazone,
5-methyl-4-phenyl-3-(phenylmethyl)-2(3H)-thiazolone-(1-methylethylidene)hydrazone, ethyl 2-[(1-methylethylidene)hydrazono]-2,3-dihydro-3-[(phenylamino)carbonyl]-4-methyl-thiazolecarboxylate,
3-methyl-4,5,6,7-tetrahydro-2(3H)-benzothiazolone-(1-methylethylidene)hydrazone,
3-methyl-2(3H)-benzothiazolone-(1-methylethylidene)hydrazone,
6-chloro-3-methyl-2(3H)-benzothiazolone-(1-methylethylidene)hydrazone,
7-chloro-3-methyl-2(3H)-benzothiazolone-(1-methylethylidene)hydrazone,
6-hydroxy-3-methyl-2(3H)-benzothiazolone-(1-methylethylidene)hydrazone,
5-methoxy-3-methyl-2(3H)-benzothiazolone-(1-methylethylidene)hydrazone,
7-methoxy-3-methyl-2(3H)-benzothiazolone-(1-methylethylidene)hydrazone,
5,6-dimethoxy-3-methyl-2(3H)-benzothiazolone-(1-methylethylidene)hydrazone,
5-ethoxy-3-methyl-2(3H)-benzothiazolone-(1-methylethylidene)hydrazone,
6-ethoxy-3-methyl-2(3H)-benzothiazolone-(1-methylethylidene)hydrazone,
3-methyl-5-nitro-2(3H)-benzothiazolone-(1-methylethylidene)hydrazone,
3-methyl-6-nitro-2(3H)-benzothiazolone-(1-methylethylidene)hydrazone,
5-acetamido-3-methyl-2(3H)-benzothiazolone-(1-methylethylidene)hydrazone,
6-acetamido-3-methyl-2(3H)-benzothiazolone-(1-methylethylidene)hydrazone,
5-anilino-3-methyl-2(3H)-benzothiazolone-(1-methylethylidene)hydrazone,
6-anilino-3-methyl-2(3H)-benzothiazolone-(1-methylethylidene)hydrazone,
2-[(1-methylethylidene)hydrazono]-2,3-dihydro-3-methyl-6-benzothazolecarboxylic acid,
2-[(1-methylethylidene)hydrazono]-2,3-dihydro-3-methyl-4-benzothiazolesulfonic acid,
2-[(1-methylethylidene)hydrazono]-2,3-dihydro-3-methyl-5-benzothiazolesulfonic acid,
2-[(1-methylethylidene)hydrazono]-2,3-dihydro-3-methyl-6-benzothiazolesulfonic acid,
2-[(1-methylethylidene)hydrazono]-2,3-dihydro-3-methyl-7-benzothiazolesulfonic acid,
2-[(1-methylethylidene)hydrazono]-2,3-dihydro-N,N,3-trimethyl-6-benzothiazole-sulfonamide,
[(2-[(1-methylethylidene)hydrazono]-2,3-dihydro-3-methyl-6-benzothiazolyl)oxy]acetic hydrazide,
3-methylnaphthol[2,3-d]thiazol-2(3H)-one-(1-methylethylidene)hydrazone,
3-ethyl-2(3H)-benzothiazolone-(1-methylethylidene)hydrazone,
6-ethoxy-3-ethyl-2(3H)-benzothiazolone-(1-methylethylidene)hydrazone,
3-propyl-2(3H)-benzothiazolone-(1-methylethylidene)hydrazone,
3-butyl-2(3H)-benzothiazolone-(1-methylethylidene)hydrazone,
3-hexyl-2(3H)-benzothiazolone-(1-methylethylidene)hydrazone,
3-hydroxyethyl-2(3H)-benzothiazolone-(1-methylethylidene)hydrazone,
3-aminoethyl-2(3H)-benzothiazolone-(1-methylethylidene)hydrazone,
3-(4-methylbenzyl)-2(3H)-benzothiazolone-(1-methylethylidene)hydrazone,
2-[(1-methylethylidene)hydrazono]-2,3-dihydro-3-(2-hydroxyethyl)-6-benzothiazole-carboxylic acid,
2-[(1-methylethylidene)hydrazono]-2,3-dihydro-6-methoxy-3(2H)-benzothiazolepro-panesulfonic acid,
6-hexadecyloxy-2-[(1-methylethylidene)hydrazono]-3(2H)-benzothiazolepropanesulfonic acid,
ethyl 2-keto-3-benzothiazolineacetate-(1-methylethylidene)hydrazone,
3-acetyl-2(3H)-benzothiazolone-(1-methylethylidene)hydrazone,
2-[(1-methylethylidene)hydrazono]-3(2H)-benzothiazolecarboxaldehyde,
3-methyl-2(3H)-oxazolone-(1-methylethylidene)hydrazone,
3-phenyl-2(3H)-oxazolone-(1-methylethylidene)hydrazone,
3-methyl-2(3H)-benzoxazolone-(1-methylethylidene)hydrazone,
3-phenyl-2(3H)-benzoxazolone-(1-methylethylidene)hydrazone,
1,3-dimethyl-4-imidazoline-2-one-(1-methylethylidene)hydrazone,
1,3-diethyl-4-imidazoline-2-one-(1-methylethylidene)hydrazone,
1,3-dihydroxyethyl-4-imidazoline-2-one-(1-methylethylidene)hydrazone,
1,3-diaminoethyl-4-imidazoline-2-one-(1-methylethylidene)hydrazone,
1,3-dimethyl-4-methoxy-4-imidazoline-2-one-(1-methylethylidene)hydrazone,
1,3,4-trimethyl-4-imidazoline-2-one-(1-methylethylidene)hydrazone,
1,3-dimethyl-4-phenyl-4-imidazoline-2-one-(1-methylethylidene)hydrazone,
4-carboxy-1,3-dimethyl-4-imidazoline-2-one-(1-methylethylidene)hydrazone,
4-amino-1,3-dimethyl-4-imidazoline-2-one-(1-methylethylidene)hydrazone,
1,3-dimethyl-4-dimethylamino-4-imidazoline-2-one-(1-methylethylidene)hydrazone,
1,3-dimethyl-2-benzimidazolinone-(1-methylethylidene)hydrazone,
1,3-diethyl-2-benzimidazolinone-(1-methylethylidene)hydrazone,
1,3-dihydroxyethyl-2-benzimidazolinone-(1-methylethylidene)hydrazone,
1,3-diaminoethyl-2-benzimidazolinone-(1-methylethylidene)hydrazone,
1,3,5-trimethyl-2-benzimidazolinone-(1-methylethylidene)hydrazone,
5-methoxy-1,3-dimethyl-2-benzimidazolinone-(1-methylethylidene)hydrazone,
5-bromo-1,3-dimethyl-2-benzimidazolinone-(1-methylethylidene)hydrazone,
4,6-dibromo-1,3-dimethyl-2-benzimidazolinone-(1-methylethylidene)hydrazone,
5-chloro-1,3-dimethyl-2-benzimidazolinone-(1-methylethylidene)hydrazone,
1,3-dimethyl-5-nitro-2-benzimidazolinone-(1-methylethylidene)hydrazone,
1,3-dimethyl-6-nitro-2-benzimidazolinone-(1-methylethylidene)hydrazone,
1,4-dimethyl-Δ2-1,2,4-triazolin-5-one-(1-methylethylidene)hydrazone,
1,4-dihydroxyethyl-Δ2-1,2,4-triazolin-5-one-(1-methylethylidene)hydrazone,
1,4-diaminoethyl-Δ2-1,2,4-triazolin-5-one-(1-methylethylidene)hydrazone, 1,3,4-trimethyl-Δ2-1,2,4-triazolin-5-one-(1-methylethylidene)hydrazone,
1,4-dimethyl-3-phenyl-Δ2-1,2,4-triazolin-5-one-(1-methylethylidene)hydrazone,
1,4-dimethyl-3-methoxy-Δ2-1,2,4-triazolin-5-one-(1-methylethylidene)hydrazone,
1,4-dimethyl-3-dimethylamino-Δ2-1,2,4-triazolin-5-one-(1-methylethylidene)hydrazone,
4-carboxy-1,4-dimethyl-Δ2-1,2,4-triazolin-5-one-(1-methylethylidene)hydrazone,
4-amino-1,4-dimethyl-Δ2-1,2,4-triazolin-5-one-(1-methylethylidene)hydrazone,
4-butyl-1-methyl-3-phenyl-Δ2-1,3,4-triazolin-5-one-(1-methylethylidene)hydrazone,
4-methyl-Δ2-1,3,4-thiadiazolin-5-one-(1-methylethylidene)hydrazone,
4-hydroxyethyl-Δ2-1,3,4-thiadiazolin-5-one-(1-methylethylidene)hydrazone,
4-aminoethyl-Δ2-1,3,4-thiadiazolin-5-one-(1-methylethylidene)hydrazone,
4-methyl-2-phenyl-Δ2-1,3,4-thiadiazolin-5-one-(1-methylethylidene)hydrazone,
2-methoxy-4-methyl-Δ2-1,3,4-thiadiazolin-5-one-(1-methylethylidene)hydrazone,
2-anilino-4-methyl-Δ2-1,3,4-thiadiazolin-5-one-(1-methylethylidene)hydrazone,
2-amino-4-methyl-Δ2-1,3,4-thiadiazolin-5-one-(1-methylethylidene)hydrazone,
2-dimethylamino-4-methyl-Δ2-1,3,4-thiadiazolin-5-one-(1-methylethylidene)hydrazone,
4-methyl-2-(methylthio)-Δ2-1,3,4-thiadiazolin-5-one-(1-methylethylidene)hydrazone,
4-(5-[(1-methylethylidene)hydrazono]-4,5-dihydro-4-methyl-Δ2-1,3,4-thiadiazol-2-yl)benzenesulfonyl fluoride,
4-methyl-Δ2-1,2,4-thiadiazolin-5-one-(1-methylethylidene)hydrazone,
4-hydroxyethyl-Δ2-1,2,4-thiadiazolin-5-one-(1-methylethylidene)hydrazone,
4-aminoethyl-Δ2-1,2,4-thiadiazolin-5-one-(1-methylethylidene)hydrazone,
4-methyl-3-phenyl-Δ2-1,2,4-thiadiazolin-5-one-(1-methylethylidene)hydrazone,
3-methoxy-4-methyl-Δ2-1,2,4-thiadiazolin-5-one-(1-methylethylidene)hydrazone,
3-amino-4-methyl-Δ2-1,2,4-thiadiazolin-5-one-(1-methylethylidene)hydrazone,
3-dimethylamino-4-methyl-Δ2-1,2,4-thiadiazolin-5-one-(1-methylethylidene)hydrazone,
3-carboxy-4-methyl-Δ2-1,2,4-thiadiazolin-5-one-(1-methylethylidene)hydrazone,
1,4-dimethyl-Δ2-1,2,4-triazolin-5-one-(1-methylethylidene)hydrazone,
1,4-dihydroxyethyl-Δ2-1,2,4-triazolin-5-one-(1-methylethylidene)hydrazone,
1,4-aminoethyl-Δ2-1,2,4-triazolin-5-one-(1-methylethylidene)hydrazone,
1,3,4-trimethyl-Δ2-1,2,4-triazolin-5-one-(1-methylethylidene)hydrazone,
1,4-dimethyl-3-phenyl-Δ2-1,2,4-triazolin-5-one-(1-methylethylidene)hydrazone, and
4-methyl-3-phenyl-Δ2-1,2,4-triazolin-5-one-(1-methylethylidene)hydrazone.

Particularly preferred) are the following compounds of formula (I):
3-methyl-2(3H)-thiazolone-(1-methylethylidene)hydrazone,
3,4-dimethyl-2(3H)-thiazolone-(1-methylethylidene)hydrazone,
4-tert.butyl-3-methyl-2(3H)-thiazolone-(1-methylethylidene)hydrazone,
3-methyl-4-phenyl-2(3H)-thiazolone-(1-methylethylidene)hydrazone,
3-methyl-4-(4-tolyl)-2(3H)-thiazolone-(1-methylethylidene)hydrazone,
4-(4-methoxy)phenyl-3-methyl-2(3H)-thiazolone-(1-methylethylidene)hydrazone,
4-(3-hydroxyphenyl)-3-methyl-2(3H)-thiazolone-(1-methylethylidene)hydrazone,
4-(4-ethoxyphenyl)-3-methyl-2(3H)-thiazolone-(1-methylethylidene)hydrazone,
4-(4-bromophenyl)-3-methyl-2(3H)-thiazolone-(1-methylethylidene)hydrazone,
4-(3-bromophenyl)-3-methyl-2(3H)-thiazolone-(1-methylethylidene)hydrazone,
4-(4chlorophenyl)-3-methyl-2(3H)-thiazolone-(1-methylethylidene)hydrazone,
4-(3chlorophenyl)-3-methyl-2(3H)-thiazolone-(1-methylethylidene)hydrazone,
3-methyl-4-(4-nitrophenyl)-2(3H)-thiazolone-(1-methylethylidene)hydrazone,
3-methyl-4-(3-nitrophenyl)-2(3H)-thiazolone-(1-methylethylidene)hydrazone,
4-[(1,1'-biphenyl]-4-yl)-3-methyl-2(3H)-thiazolone-(1-methylethylidene)hydrazone,
ethyl 2-[(1-methylethylidene)hydrazono]-2,3-dihydro-3-methyl-4-thiazolecarboxylate,
3,4,5-trimethyl-2(3H)-thiazolone-(1-methylethylidene)hydrazone,
3,4-dimethyl-5-phenyl-2(3H)-thiazolone-(1-methylethylidene)hydrazone,
3,5-dimethyl-4-phenyl-2(3H)-thiazolone-(1-methylethylidene)hydrazone,
3-methyl-4,5-diphenyl-2(3H)-thiazolone-(1-methylethylidene)hydrazone,
5-ethyl-3-methyl-4-phenyl-2(3H)-thiazolone-(1-methylethylidene)hydrazone,
4-(4-bromophenyl)-3-methyl-5-phenyl-2(3H)-thiazolone-(1-methylethylidene)hydrazone,
3-methyl-5-phenyl-4-(4-tolyl)-2(3H)-thiazolone-(1-methylethylidene)hydrazone,
5-(4-chlorophenyl)-4-phenyl-3-methyl-2(3H)-thiazolone-(1-methylethylidene)hydrazone,
5-(4-chlorophenyl)-4-(4-methoxyphenyl)-3-methyl-2(3H)-thiazolone-(1-methylethylidene)hydrazone,
ethyl 2-[(1-methylethylidene)hydrazono]-2,3-dihydro-3,4-dimethyl-4-thiazolecar-boxylate,
4-amino-2-[(1-methylethylidene)hydrazono]-2,3-dihydro-3-methyl-5-thiazolecarbonitrile,
3-ethyl-4,5-dimethyl-2(3H)-thiazolone-(1-methylethylidene)hydrazone,
ethyl 2-[(1-methylethylidene)hydrazono]-2,3-dihydro-3-ethyl-4-methylthiazolecarboxylate,
5-methyl-3-(1-methylethyl)-4-phenyl-2(3H)-thiazolone-(1-methylethylidene)hydrazone,
4,5-dimethyl-3-(1-methylethyl)-2(3H)-thiazolone-(1-methylethylidene)hydrazone,
3-(1-methylethyl)-4,5-diphenyl-2(3H)-thiazolone-(1-methylethylidene)hydrazone,
4-methyl-3-propyl-2(3H)-thiazolone-(1-methylethylidene)hydrazone,
4,5-dimethyl-3-propyl-2(3H)-thiazolone-(1-methylethylidene)hydrazone, 4,5-diphenyl-3-propyl-2(3H)-thiazolone-(1-methylethylidene)hydrazone,
3-butyl-4,5-dimethyl-2(3H)-thiazolone-(1-methylethylidene)hydrazone,
3-butyl-4,5-diphenyl-2(3H)-thiazolone-(1-methylethylidene)hydrazone,
4,4-dimethyl-3-(2-methylpropyl)-2(3H)-thiazolone-(1-methylethylidene)hydrazone,
3-(2-methylpropyl)-4,5-diphenyl-2(3H)-thiazolone-(1-methylethylidene)hydrazone,
3-allyl-2(3H)-thiazolone-(1-methylethylidene)hydrazone,
3-allyl-4-methyl-2(3H)-thiazolone-(1-methylethylidene)hydrazone,
3-allyl-4-tert.butyl-2(3H)-thiazolone-(1-methylethylidene)hydrazone,
3-allyl-4-phenyl-2(3H)-thiazolone-(1-methylethylidene)hydrazone,
3-allyl-4,5-dimethyl-2(3H)-thiazolone-(1-methylethylidene)hydrazone,
3-allyl-4,5-diphenyl-2(3H)-thiazolone-(1-methylethylidene)hydrazone,
3-hydroxyethyl-2(3H)-thiazolone-(1-methylethylidene)hydrazone,
3-hydroxyethyl-4-methyl-2(3H)-thiazolone-(1-methylethylidene)hydrazone,
3-hydroxyethyl-4,5-dimethyl-2(3H)-thiazolone-(1-methylethylidene)hydrazone,
3-aminoethyl-2(3H)-thiazolone-(1-methylethylidene)hydrazone,
3-aminoethyl-4-methyl-2(3H)-thiazolone-(1-methylethylidene)hydrazone,
3-aminoethyl-4,5-dimethyl-2(3H)-thiazolone-1-methylethylidene)hydrazone,
3-phenyl-2(3H)-thiazolone-(1-methylethylidene)hydrazone,
3,4-diphenyl-2(3H)-thiazolone-(1-methylethylidene)hydrazone,
4-methyl-3-phenyl-2(3H)-thiazolone-(1-methylethylidene)hydrazone,
4-p-biphenylyl-3-phenyl-2(3H)-thiazolone-(1-methylethylidene)hydrazone,
4-(4-methoxy)phenyl-3-phenyl-2(3H)-thiazolone-(1-methylethylidene)hydrazone,
4-tert.butyl-3-phenyl-2(3H)-thiazolone-(1-methylethylidene)hydrazone,
4,5-dimethyl-3-phenyl-2(3H)-thiazolone-(1-methylethylidene)hydrazone,
5-methyl-3,4-diphenyl-2(3H)-thiazolone-(1-methylethylidene)hydrazone,
3,4,5-triphenyl-2(3H)-thiazolone-(1-methylethylidene)hydrazone,
4,5-dimethyl-3-(phenylmethyl)-2(3H)-thiazolone-(1-methylethylidene)hydrazone,
4-phenyl-3-(phenylmethyl)-2(3H)-thiazolone-(1-methylethylidene)hydrazone,
5-methyl-4-phenyl-3-(phenylmethyl)-2(3H)-thiazolone-(1-methylethylidene)hydrazone,
3-methyl-4,5,6,7-tetrahydro-2(3H)-benzothiazolone-(1-methylethylidene)hydrazone,
3-methyl-2(3H)-benzothiazolone-(1-methylethylidene)hydrazone,
3,6-dimethyl-2(3H)-benzothiazolone-(1-methylethylidene)hydrazone,
6-chloro-3-methyl-2(3H)-benzothiazolone-(1-methylethylidene)hydrazone,
7-chloro-3-methyl-2(3H)-benzothiazolone-(1-methylethylidene)hydrazone,
6-hydroxy-3-methyl-2(3H)-benzothiazolone-(1-methylethylidene)hydrazone,
5-methoxy-3-methyl-2(3H)-benzothiazolone-(1-methylethylidene)hydrazone,
7-methoxy-3-methyl-2(3H)-benzothiazolone-(1-methylethylidene)hydrazone,
5,6-dimethoxy-3-methyl-2(3H)-benzothiazolone-(1-methylethylidene)hydrazone,
5-ethoxy-3-methyl-2(3H)-benzothiazolone-(1-methylethylidene)hydrazone,
6-ethoxy-3-methyl-2(3H)-benzothiazolone-(1-methylethylidene)hydrazone,
3-methyl-5-nitro-2(3H)-benzothiazolone-(1-methylethylidene)hydrazone,
3-methyl-6-nitro-2(3H)-benzothiazolone-(1-methylethylidene)hydrazone,
5-acetamido-3-methyl-2(3H)-benzothiazolone-(1-methylethylidene)hydrazone,
6-acetamido-3-methyl-2(3H)-benzothiazolone-(1-methylethylidene)hydrazone,
5-anilino-3-methyl-2(3H)-benzothiazolone-(1-methylethylidene)hydrazone,
6-anilino-3-methyl-2(3H)-benzothiazolone-(1-methylethylidene)hydrazone,
2-[(1-methylethylidene)hydrazono]-2,3-dihydro-3-methyl-6-benzothiazolecarboxylic acid,
2-[(1-methylethylidene)hydrazono]-2,3-dihydro-3-methyl-4-benzothiazolesulfonic acid,
2-[(1-methylethylidene)hydrazono]-2,3-dihydro-3-methyl-5-benzothiazolesulfonic acid,
2-[(1-methylethylidene)hydrazono]-2,3-dihydro-3-methyl-6-benzothiazolesulfonic acid,
2-[(1-methylethylidene)hydrazono]-2,3-dihydro-3-methyl-7-benzothiazolesulfonic acid,
2-[(1-methylethylidene)hydrazono]-2,3-dihydro-N,N-3-trimethyl-6-benzothiazolesulfonamide,
[(2-[(1-methylethylidene)hydrazono]-2,3-dihydro-3-methyl-4-benzothiazolyl)oxy]acetic hydrazide,
3-ethyl-2(3H)-benzothiazolone-(1-methylethylidene)hydrazone,
6-ethoxy-3-ethyl-2(3H)-benzothiazolone-(1-methylethylidene)hydrazone,
3-propyl-2(3H)-benzothiazolone-(1-methylethylidene)hydrazone,
3-butyl-2(3H)-benzothiazolone-(1-methylethylidene)hydrazone and
3-hexyl-2(3H)-benzothiazolone-(1-methylethylidene)hydrazone.

The compounds of formula (I) can be prepared by methods of synthesis known from the literature, for example by the method described in Research Disclosure October 1978, pages 42-44 (1978), No. 17434.

Particularly suitable couplers are the following substances or the salts thereof:
N-(3-dimethylaminophenyl)urea, 2,6-diaminopyridine, 2-amino-4-[(2-hydroxyethyl)amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 1,3-diamino-4-(2,3-dihydroxypropoxy)benzene, 1,3-diamino-4-(3-hydroxypropoxy)benzene, 1,3-diamino-4-(2- methoxyethoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethyl-aminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methyl-phenol, 1-naphthol, 2-methyl-1-naphthol, 1,5-dihydroxynaphthalene, 1,7-dihydroxy-naphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxy-benzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Suitable persulfate salts are, for example, potassium persulfate, sodium persulfate or ammonium persulfate and a mixture thereof.

The ready-to-use colorant (A) contains the persulfate salts in a total amount from about 0.01 to 10 weight percent and preferably from about 0.1 to 5 weight percent.

In addition to the compounds of formula (I) and the coupler, the colorant of the invention can optionally also contain other common, physiologically harmless direct dyes from the group of cationic and anionic dyes, disperse dyes, azo dyes, quinone dyes and tri-phenylmethane dyes.

The ready-to-use colorant (A) contains the direct dyes in an amount from about 0.01 to 10 weight percent and preferably from about 0.1 to 5 weight percent.

In addition to the compounds of formula (I), the colorant of the invention can optionally also contain common developers, for example 1,4-diaminobenzene (p-phenylenediamine), 1,4-diamino-2-methylbenzene (p-toluylenediamine), 1,4-diamino-2-(thiophen-2-yl)benzene, 1,4-diamino-2-thiophen-3-yl)benzene, 4-(2,5-diaminophenyl)-2-[(diethylamino)methyl]thiophene, 2-chloro-3-(2,5-diaminophenyl)thiophene, 1,4-diamino-2-(pyridin-3-yl)benzene, 2,5-diaminobiphenyl, 2,5-diamino-4'-(1-methylethyl)-1,1'-biphenyl, 2,3',5-triamino-1,1'-biphenyl, 1,4-diamino-2-methoxymethylbenzene, 1,4-diamino-2-aminomethylbenzene, 1,4-diamino-2-[(phenylamino) methyl]benzene, 1,4-diamino-2{[ethyl-(2-hydroxyethyl)amino]methyl}benzene, 1,4-diamino-2-hydroxymethylbenzene, 4-[di(2-hydroxyethyl)amino]aniline, 4-{[(4-aminophenyl)methyl]amino}aniline, 4-[(4-aminophenylamino)methyl]phenol, 1,4-diamino-N-(4-pyrrolidin-1-ylbenzyl)benzene, 1,4-diamino-N-furan-3-ylmethylbenzene, 1,4-diamino-N-thiophen-2-ylmethylbenzene, 1,4-diamino-N-furan-2-ylmethylbenzene, 1,4-diamino-N-thiophen-3-ylmethylbenzene, 1,4-diamino-N-benzylbenzene, 1,4-diamino-2-(1-hydroxyethyl)-benzene, 1,4-diamino-2-(2-hydroxyethyl)benzene, 1,3-bis-[(4-aminophenyl)(2-hydroxyethyl)amino]-2-propanol, 1,8-bis-(2,5-diaminophenoxy)-3,6-dioxaoctane, 2,5-diamino-4'-hydroxy-1,1'-biphenyl, 2,5-diamino-2'-trifluoromethyl-1,1'-biphenyl, 2,4',5-triamino-1,1'-bi-phenyl, 4-aminophenol, 4-amino-3-methylphenol, 4-methylaminophenol, 4-amino-2-(amino-methyl)phenol, 4-amino-2-[(2-hydroxyethyl)amino]methylphenol, 4-amino-2-(methoxymethyl)phenol, 5-aminosalicylic acid, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-pentyl-1H-pyrazole, 4,5-diamino-1-(phenylmethyl)-1H-pyrazole, 4,5-diamino-1-(4-methoxyphenyl)methyl-1H-pyrazole, 2-aminophenol, 2-amino-6-methylphenol, 2-amino-5-methylphenol, 1,2,4-trihydroxybenzene, 2,4-diaminophenol, 1,4-dihydroxybenzene or 2-{[(4-aminophenyl)amino]methyl}-1,4-diaminobenzene.

The compounds of formula (I) and the couplers and additional developers are contained in the ready-to-use colorant (A) in a total amount from about 0.01 to 10 weight percent and preferably from about 0.1 to 5 weight percent, each.

As a rule, the compounds of formula (I) and the couplers are stored separately and just before use are mixed with one another, and the persulfate salt is added to them. If the compounds of formula (I), the couplers and the persulfate salt are solids, however, it is also possible to package them together and shortly before use to prepare the ready-to-use colorant (A) by mixing the compounds of formula (I), the couplers and the persulfate salt with water or with a liquid preparation containing the other ingredients of the agent.

As a rule, the colorant of the invention consists therefore of several components that are to be mixed before use. The agent is preferably in the form of a 2-component kit consisting of a dye carrier composition (A1) containing the compound of formula (I) and another dye carrier composition (A2) containing the couplers and the persulfate salts, or of a 3-component kit consisting of a dye carrier composition (A1) containing the compound of formula (I), another dye carrier composition (A2) containing the couplers, and a third component (A3) containing the persulfate salts.

Another object of the present invention is a multicomponent kit consisting of an agent of component (A1) and an agent of component (A2), the persulfate possibly being packaged as component (A3) separately from component (A2), and optionally of a pH-adjusting agent (alkalinizing agent or acid). Naturally, the agents of components (A1) and (A2) can also consist of several individual components to be mixed only just before use. Also possible is a 2-component kit with a first component that consists of one of the compounds of formula (I), the coupler and the persulfate salts and optionally other powders containing other common powdered cosmetic additives, and with a second component that consists of water or of a liquid cosmetic preparation. Particularly preferred, however, is a 2-component kit consisting of an agent of component (A1) and an agent of component (A2).

The aforementioned direct dyes can be used in component (A1) and/or component (A2) in a total amount from about 0.02 to 20 weight percent and preferably from 0.2 to 10 weight percent, whereas each of the couplers and additional developers can be contained in the dye carrier component [component (A1) or component (A2)] in a total amount from about 0.02 to 20 weight percent and preferably from about 0.2 to 10 weight percent.

Components (A1) and (A2) as well as the ready-to-use colorant (A) can be formulated, for example, as a solution, particularly an aqueous or aqueous-alcoholic solution, or as a cream, a gel or an emulsion. The preparations consist of a mixture of the compound of formula (I) or of the couplers with additives commonly used in such preparations.

Additives that are commonly used in colorants in the form of solutions, creams, emulsions, gels or aerosol foams are, for example, solvents such as water, lower aliphatic alcohols, for example ethanol, n-propanol and isopropanol or glycols such as glycerol and 1,2-propanediol, moreover wetting agents or emulsifiers from the classes of anionic, cationic, amphoteric or nonionic surface-active substances, such as the fatty alcohol sulfates, ethoxylated fatty alcohol sulfates, alkylsulfonates, alkylbenzenesulfonates, alkyltrimethyl-ammonium salts, alkylbetaines, ethoxylated fatty alcohols, ethoxylated nonylphenols, fatty alkanolamides, ethoxylated fatty esters, furthermore thickeners such as the higher fatty alcohols, starch or cellulose derivatives, perfumes, hair pretreatment agents, conditioners, hair swelling agents, preservatives, moreover vaseline, paraffin oil and fatty acids and also hair-care agents such as cationic resins, lanolin derivatives, cholesterol, pantothenic acid and betaine. The said constituents are employed in amounts commonly used for such purposes, for example the wetting agents and emulsifiers at a concentration from about 0.5 to 30 weight percent [always based on component (A1) or (A2)], the thickeners in an amount from about 0.1 to 25 wt. % [always based on component (A1) or (A2)] and the hair-care agents at a concentration from about 0.1 to 5.0 weight percent [always based on component (A1) or (A2)].

The pH of the ready-to-use colorant (A) and of the dye carrier compositions (A1) and (A2) is about 3 to 12 and preferably about 6 to 10, the pH of the ready-to-use colorant (A) as a rule being adjusted by mixing component (A1) with component (A2) and optionally with the persulfates. To adjust the pH of components (A1) and (A2) and of the ready-to-use colorant (A) to the value desired for coloring, however, it is also possible, if needed, to use alkalinizing agents, for example ammonia, alkali metal hydroxides, alkaline earth metal hydroxides, alkali metal acetates, alkaline earth metal acetates, alkali metal carbonates or alkaline earth metal carbonates, or else acids, for example lactic acid, acetic acid, tartaric acid, phosphoric acid, hydrochloric acid, citric acid, ascorbic acid or boric acid.

The ready-to-use colorant is prepared just before use by mixing components (A1) and (A2) or (A1), (A2) and (A3)—optionally adding an alkalinizing agent or an acid—and then applying the mixture to the fibers, particularly human hair. Depending on the color depth desired, said mixture is allowed to act on the hair for about 5 to 60 minutes and preferably for about 15 to 30 minutes at a temperature from about 20 to 50° C. and particularly from about 30 to 40° C. The fibers are then rinsed with water, optionally washed with a shampoo and then dried.

The colorant of the invention produces a uniform and lasting coloration of the fibers, particularly keratin fibers, for example human hair. A wide range of yellow to blue color shades can thus be obtained. Resistance to perspiration is achieved to a particularly high degree.

The following examples will explain the subject matter of the invention in greater detail without limiting its scope.

EXAMPLES

Example 1

Synthesis of 3,4-dimethyl-2(3H)-thiazolone-1-methylethylidene)-hydrazone

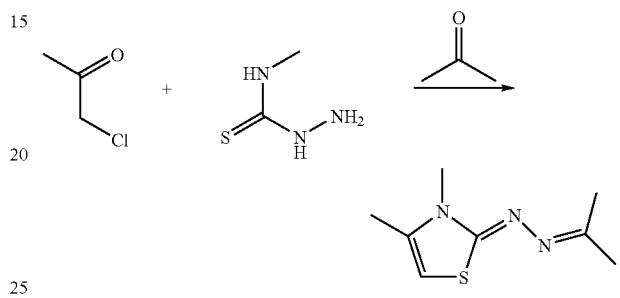

21 g (200 mmoles) of 4-methyl-3-thiosemicarbazide in 1000 mL of acetone was heated under reflux for 2 hours. To the solution was then added dropwise 20.4 g (220 mmoles) of chloroacetone. The reaction mixture was allowed to reflux for 7 hours after which it was concentrated. The crude product thus obtained was recrystallized from acetone. This gave 23 g of an orange powder (63% of the theoretical).

Melting point 139-139.6° C.

$^1$H-NMR (DMSO, 300 MHz): δ=6.72 [s, broad, 1H, H—C(5)]; δ=3.67 (s, 3H, N—CH3); δ=2.27 [d, J=0.9 Hz, 3H, CH3—C(4)]; δ=2.17 (s, 3H, CH3); δ=2.07 (s, 3H, CH3).

$^{13}$C-NMR (DMSO 300 MHz): δ=169.16; δ=164.14; δ=139.02 [C(4)]; δ=103.36 [C(5)]; δ=34.47 (CH$_3$N); δ=24.60; δ=19.91; δ=13.53 [CH$_3$—C(4)].

MS(ESI): 184 [M+H]$^+$ (100).

Examples 2-9

Synthesis of Derivatives of Formula (I) (General Method of Synthesis)

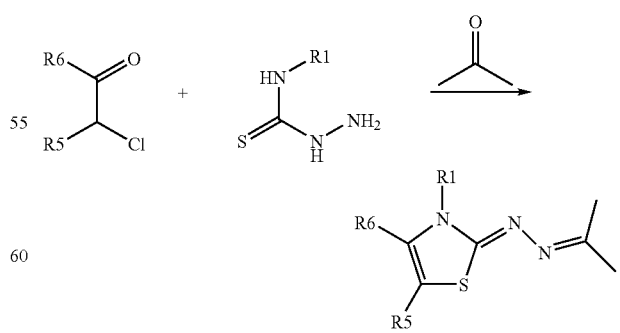

4 mmoles of substituted thiosemicarbazide in 20 mL of acetone was heated under reflux for 2 hours. To the solution was then added dropwise 4.4 mmoles of an α-chloroketone.

The reaction mixture was heated under reflux for 7 hours and then concentrated. The resulting 2(3H)-thiazolone-1-(methylethylidene)hydrazone was recrystallized from acetone.

2. 3-Methyl-4-phenyl-2(3H)-thiazolone-1-(methylethylidene)hydrazone

From 4-methyl-3-thiosemicarbazide and phenacyl chloride.
Yield: 1 g (100% of the theoretical)
ESI-MS: 246 [M+H]$^+$ (100)

3. 4-tert Butyl-3-methyl-2(3H)-thiazolone-1-(methylethylidene)hydrazone

From 4-methyl-3-thiosemicarbazide and 1-chloro-3,3-dimethyl-2-butanone
Yield: 0.67 g (75% of the theoretical)
ESI-MS: 226 [M+H]$^+$ (100)

4. 3-Allyl-4-methyl-2(3H)-thiazolone-1-(methylethylidene)hydrazone

From 4-allyl-3-thiosemicarbazide and chloroacetone
Yield: 0.32 g (39% of the theoretical)
ESI-MS: 210 [M+H]$^{+/}$ (100)

5. 3-Allyl-4-phenyl-2(3H)-thiazolone-1-(methylethylidene)hydrazone

From 4-allyl-3-thiosemicarbazide and phenacyl chloride
Yield: 0.57 g (53% of the theoretical)
ESI-MS: 272 [M+H]$^+$ (100)

6. 3-Allyl-4-tert butyl-2(3H)-thiazolone-1-(methylethylidene)hydrazone

From 4-allyl-3-thiosemicarbazide and 1-chloro-3,3-dimethyl-2-butanone
Yield: 0.53 g (53% of the theoretical)
ESI-MS: 252 [M+H]$^+$ (100)

7. 3,4-Diphenyl-2(3H)-thiazolone-1-(methylethylidene)hydrazone

From 4-phenyl-3-thiosemicarbazide and phenacyl chloride
Yield: 0.83 g (68% of the theoretical)
ESI-MS: 308 [M+H]$^+$ (100)

8. Ethyl{2-[(1-methylethylidene)hydrozone]-3-phenyl-2,3-dihydro-1,3-thiazol-4-yl}-acetat From 4-phenyl-3-thiosemicarbazide and ethyl 4-chloroacetate
Yield: 0.34 g (27% of the theoretical)
ESI-MS: 318 [M+H]$^+$ (100)

9. 3,4,5-Trimethyl-2(3H)-thiazolone-1-(methylethylidene)hydrazone

From 4-methyl-3-thiosemicarbazide and 3-chloro-2-butanone
Yield: 0.27 g (34% of the theoretical)
ESI-MS: 198 [M+H]$^+$ (100)

Examples 10-15

Colorants with 3,4-dimethyl-2(3H)-thiazolone-1-(methylethylidene)hydrazone

| Component (A1) | |
|---|---|
| 4.00 g | of decylpolyglucose (Plantaren ® 2000), 50% aqueous solution |
| 0.20 g | disodium ethylenediaminetetraacetate hydrate |
| 5.00 g | of ethanol |
| 0.46 g | of 3,4-dimethyl-2(3H)-thiazolone-1-(methylethylidene) hydrazone |
| to 100.00 g | water, demineralized |
| Component (A2) | |
| Y g | of coupler as per Table 1 |
| 0.80 g | of potassium persulfate |

The afore-mentioned components (A1) and (A2) were uniformly mixed with one another at room temperature (20-25° C.) or with slight heating (35-40° C.) If necessary, the pH of the resulting ready-to-use colorant (A) was adjusted to the value indicated in Table 1 with sodium hydroxide, sodium carbonate or ammonia.

The ready-to-use hair colorant was applied to bleached buffalo hair and uniformly distributed with a brush. After an exposure time of 30 minutes at 40° C., the hair was washed with a commercial shampoo and then dried.

The amount of coupler used and the coloration obtained are summarized in the following Table 1.

TABLE 1

| Example No. | Coupler used (amount in g) | pH | Color Shade |
|---|---|---|---|
| 10 | 1,3-diaminobenzene (0.27 g) | 9.9 | Bordeaux red |
| 11 | 2,4-diamino-1-(2-hydroxyethoxy)-benzene sulfate (0.67 g) | 10.0 | dark brown-violet |
| 12 | N-(3-dimethylaminophenyl)urea (0.44 g) | 9.5 | blue |
| 13 | 3-aminophenol (0.27 g) | 9.6 | strawberry red |
| 14 | 5-amino-2-methylphenol (0.31 g) | 9.6 | red-orange |
| 15 | 1,3-dihydroxybenzene (0.27 g) | 9.0 | red |

Examples 16-55

Colorants with 2(3H)-thiazolone-1-(methylethylidene)hydrazones of formula (I)

| Component (A1) | |
|---|---|
| 4.00 g | of decylpolyglucose (Plantaren ® 2000), 50% aqueous solution |
| 0.20 g | of disodium ethylenediaminetetraacetate hydrate |
| 5.00 g | of ethanol |
| X g | of 2(3H)-thiazolone-1-(methylethylidene)hydrazone of formula (I) |
| to 100.00 g | water, demineralized |
| Component (A2) | |
| Y g | of coupler as per Table 2 |
| 0.80 g | of potassium persulfate |

The afore-mentioned components (A1) and (A2) were uniformly mixed with one another at room temperature (20-25° C.) or with slight heating (35-40° C.). If necessary, the pH of the resulting ready-to-use colorant (A) was adjusted to the value indicated in Table 2 with sodium hydroxide, sodium carbonate or ammonia.

The ready-to-use hair colorant was applied to bleached hair and uniformly distributed with a brush. After an exposure time of 30 minutes at 40° C., the hair was washed with a commercial shampoo and then dried.

The amount of 2(3H)-thiazolone-1-(methylethylidene)hydrazones of formula (I) and of the coupler used as well as the coloration obtained are summarized in the following Table 2.

TABLE 2

| Example No. | Derivative of Formula (I) as per Example No. (amount in g) | Coupler Used (amount in g) | pH | Color Shade |
| --- | --- | --- | --- | --- |
| 16 | Example 2 (0.61 g) | 1,3-diaminobenzene (0.27 g) | 9.6 | Bordeaux red |
| 17 | Example 3 (0.56 g) | 1,3-diaminobenzene (0.27 g) | 9.6 | Bordeaux red |
| 18 | Example 4 (0.52 g) | 1,3-diaminobenzene (0.27 g) | 9.6 | Bordeaux red |
| 19 | Example 5 (0.68 g) | 1,3-diaminobenzene (0.27 g) | 9.6 | light Bordeaux red |
| 20 | Example 6 (0.63 g) | 1,3-diaminobenzene (0.27 g) | 9.6 | Bordeaux red |
| 21 | Example 7 (0.77 g) | 1,3-diaminobenzene (0.27 g) | 9.6 | gray beige |
| 22 | Example 8 (0.79 g) | 1,3-diaminobenzene (0.27 g) | 9.6 | light Bordeaux red |
| 23 | Example 9 (0.49 g) | 1,3-diaminobenzene (0.27 g) | 9.6 | Bordeaux red |
| 24 | Example 2 (0.61 g) | 2,4-diamino-1-(2-hydroxyethoxy)benzene sulfate (0.67 g) | 9.6 | dark Bordeaux red |
| 25 | Example 3 (0.56 g) | 2,4-diamino-1-(2-hydroxyethoxy)benzene sulfate (0.67 g) | 9.6 | dark Bordeaux red |
| 26 | Example 4 (0.52 g) | 2,4-diamino-1-(2-hydroxyethoxy)benzene sulfate (0.67 g) | 9.6 | dark Bordeaux red |
| 27 | Example 5 (0.68 g) | 2,4-diamino-1-(2-hydroxyethoxy)benzene sulfate (0.67 g) | 9.6 | dark Bordeaux red |
| 28 | Example 6 (0.63 g) | 2,4-diamino-1-(2-hydroxyethoxy)benzene sulfate (0.67 g) | 9.6 | dark Bordeaux red |
| 29 | Example 7 (0.77 g) | 2,4-diamino-1-(2-hydroxyethoxy)benzene sulfate (0.67 g) | 9.6 | brown |
| 30 | Example 8 (0.79 g) | 2,4-diamino-1-(2-hydroxyethoxy)benzene sulfate (0.67 g) | 9.6 | dark Bordeaux red |
| 31 | Example 9 (0.49 g) | 2,4-diamino-1-(2-hydroxyethoxy)benzene sulfate (0.67 g) | 9.6 | dark Bordeaux red |
| 32 | Example 2 (0.61 g) | N-(3-dimethylaminophenyl)urea (0.44 g) | 9.5 | light blue |
| 33 | Example 3 (0.56 g) | N-(3-dimethylaminophenyl)urea (0.44 g) | 9.5 | light blue |
| 34 | Example 4 (0.52 g) | N-(3-dimethylaminophenyl)urea (0.44 g) | 9.5 | blue |
| 35 | Example 5 (0.68 g) | N-(3-dimethylaminophenyl)urea (0.44 g) | 9.5 | light blue |
| 36 | Example 6 (0.63 g) | N-(3-dimethylaminophenyl)urea (0.44 g) | 9.5 | light blue |
| 37 | Example 7 (0.77 g) | N-(3-dimethylaminophenyl)urea (0.44 g) | 9.5 | very light blue |
| 38 | Example 8 (0.79 g) | N-(3-dimethylaminophenyl)urea (0.44 g) | 9.5 | light blue |
| 39 | Example 9 (0.49 g) | N-(3-dimethylaminophenyl)urea (0.44 g) | 9.5 | light blue |
| 40 | Example 2 (0.61 g) | 3-aminophenol (0.27 g) | 9.6 | dark blond |
| 41 | Example 3 (0.56 g) | 3-aminophenol (0.27 g) | 9.6 | strawberry red |
| 42 | Example 4 (0.52 g) | 3-aminophenol (0.27 g) | 9.6 | strawberry red |
| 43 | Example 5 (0.68 g) | 3-aminophenol (0.27 g) | 9.6 | copper-brown |

TABLE 2-continued

| Example No. | Derivative of Formula (I) as per Example No. (amount in g) | Coupler Used (amount in g) | pH | Color Shade |
|---|---|---|---|---|
| 44 | Example 6 (0.63 g) | 3-aminophenol (0.27 g) | 9.6 | strawberry red |
| 45 | Example 7 (0.77 g) | 3-aminophenol (0.27 g) | 9.6 | brown |
| 46 | Example 8 (0.79 g) | 3-aminophenol (0.27 g) | 9.6 | light strawberry red |
| 47 | Example 9 (0.49 g) | 3-aminophenol (0.27 g) | 9.6 | strawberry red |
| 48 | Example 2 (0.61 g) | 1,3-dihydroxybenzene (0.27 g) | 10.0 | light red-orange |
| 49 | Example 3 (0.56 g) | 1,3-dihydroxybenzene (0.27 g) | 10.0 | light red-orange |
| 50 | Example 4 (0.52 g) | 1,3-dihydroxybenzene (0.27 g) | 10.0 | red-orange |
| 51 | Example 5 (0.68 g) | 1,3-dihydroxybenzene (0.27 g) | 10.0 | very light red-orange |
| 52 | Example 6 (0.63 g) | 1,3-dihydroxybenzene (0.27 g) | 10.0 | red-orange |
| 53 | Example 7 (0.77 g) | 1,3-dihydroxybenzene (0.27 g) | 10.0 | beige |
| 54 | Example 8 (0.79 g) | 1,3-dihydroxybenzene (0.27 g) | 10.0 | light red-orange |
| 55 | Example 9 (0.49 g) | 1,3-dihydroxybenzene (0.27 g) | 10.0 | red-orange |

Unless otherwise indicated, all percentages given in the present patent application are by weight.

What is claimed is:

1. A fiber-coloring agent (A), containing
   a) at least one hydrazone derivative of formula (I), or a physiologically compatible salt thereof:

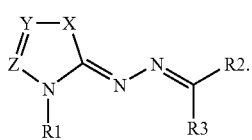

(I)

in which X denotes oxygen, sulfur, or N—R4;
Y denotes C—R5 or nitrogen, and
Z denotes C—R6 or nitrogen;
provided that a heterocyclic part of the derivative of the formula (I) contains at the most three heteroatoms;
in which R1 and R4 are equal or different and, independently of each other, each denote a saturated or unsaturated $(C_1$-$C_{12})$-alkyl group, a $(C_1$-$C_{12})$-alkyl group substituted with a halogen atom, a hydroxy-$(C_1$-$C_{12})$-alkyl group, an amino-$(C_1$-$C_{12})$-alkyl group, a $(C_1$-$C_{12})$-alkylsulfonic acid group, a formyl group, a C(O)-$(C_1$-$C_{12})$-alkyl group, a C(O)-phenyl group, a C(O) NH—$(C_1$-$C_{12})$-alkyl group, a C(O)NH-phenyl group, a substituted or unsubstituted phenyl group, or a benzyl group;
R2 and R3 are equal or different and, independently of each other, each denote a saturated or unsaturated $(C_1$-$C_{12})$-alkyl group;
R5 and R6 are equal or different and, independently of each other, each denote hydrogen, a halogen atom, a saturated or unsaturated $(C_1$-$C_{12})$-alkyl group, a $(C_1$-$C_{12})$-alkyl group substituted with a halogen atom, a $(C_1$-$C_{12})$-hydroxyalkyl group, a $(C_1$-$C_{12})$-alkoxy group, a cyano group, a nitro group, an amino group, a $(C_1$-$C_{12})$-alkylamino group, a $(C_1$-$C_{12})$-dialkylamino group, a carboxylic acid group, a C(O)O-$(C_1$-$C_{12})$-alkyl group, a substituted or unsubstituted C(O)O-phenyl group, a substituted or unsubstituted phenyl group, or a naphthyl group;
and with the proviso that, if Y and Z denote said C—R3 and said C—R4, then R5 and R6 together with a remainder of the formula (I) form a heterocyclic or carbocyclic, saturated or unsaturated, substituted or unsubstituted ring system;
(b) at least one coupler, or a physiologically compatible salt thereof; and
(c) a persulfate salt as oxidant.

2. The agent as defined in claim 1, in which X denotes said sulfur, Y and Z denote said C—R5 and said C—R6 respectively, and R2 and R3 each denote a methyl group.

3. The agent as defined in claim 1 in which the at least one hydrazone derivative of the formula (I) is selected from the group consisting of
   3-methyl-2(3H)-thiazolone-(1-methylethylidene)hydrazone,
   3,4-dimethyl-2(3H)-thiazolone-(1-methylethylidene)hydrazone,
   4-tert.-butyl-3-methyl-2(3H)-thiazolone-(1-methylethylidene)hydrazone,
   3-methyl-4-phenyl-2(3H)-thiazolone-(1-methylethylidene)hydrazone,
   3-methyl-4-(4-tolyl)-2(3H)-thiazolone-(1-methylethylidene)hydrazone,
   4-(4-methoxy)-phenyl-3-methyl-2(3H)-thiazolone-(1-methylethylidene)hydrazone,
   4-(3-hydroxyphenyl)-3-methyl-2(3H)-thiazolone-(1-methylethylidene)hydrazone,
   4-(4-ethoxyphenyl)-3-methyl-2(3H)-thiazolone-(1-methylethylidene)hydrazone,
   4-(4-bromophenyl)-3-methyl-2(3H)-thiazolone-(1-methylethylidene)hydrazone, 4-(3-bromophenyl)-3-methyl-2(3H)-thiazolone-(1-methylethylidene)hydrazone,
4-(4-chlorophenyl)-3-methyl-2(3H)-thiazolone-(1-methylethylidene)hydrazone,
4-(3-chlorophenyl)-3-methyl-2(3H)-thiazolone-(1-methylethylidene)hyd razone,
3-methyl-4-(4-nitrophenyl)-2(3H)-thiazolone-(1-methylethylidene)hydrazone,
3-methyl-4-(3-nitrophenyl)-2(3H)-thiazolone-(1-methylethylidene)hydrazone,
4-[(1,1-biphenyl]-4-yl)-3-methyl-2(3H)-thiazolone-(1-methylethylidene)hydrazone,
ethyl 2-[(1-methylethylidene)hydrazono]-2,3-dihydro-3-methyl-4-thiazolecarboxylate,
3,4,5-trimethyl-2(3H)-thiazolone-(1-methylethylidene) hyd razone,
3,4-dimethyl-5-phenyl-2(3H)-thiazolone-(1-methylethylidene)hydrazone,
3,5-dimethyl-4-phenyl-2(3H)-thiazolone-(1-methylethylidene)hydrazone,
3-methyl-4,5-diphenyl-2(3H)-thiazolone-(1-methylethylidene)hydrazone,
5-ethyl-3-methyl-4-phenyl-2(3H)-thiazolone-(1-methylethylidene)hydrazone,
4-(4-bromophenyl)-3-methyl-5-phenyl-2(3H)-thiazolone-(1-methylethylidene)-hydrazone,
3-methyl-5-phenyl-4-(4-tolyl)-2(3 H )-thiazolone-(1-methylethylidene)hyd razone,
5-(4-chlorophenyl )-4-phenyl-3-methyl-2(3H )-thiazolone-(1-methylethylidene)-hydrazone,
5-(4-chlorophenyl)-4-(4-methoxyphenyl)-3-methyl-2(3H )-thiazolone-(1-methyl-ethylidene)hydrazone,
ethyl 2-[(1-methylethylidene)hydrazono]-2,3-dihydro-3,4-dimethyl-4-thiazole carboxylate,
4-amino-2-[(1-methylethylidene)hydrazono]-2,3-dihydro-3-methyl-5-thiazole carbonitrile,
3-ethyl-4,5-dimethyl-2(3H )-thiazolone-(1-methylethylidene)hydrazone, ethyl 2-[(1-methylethylidene)hydrazono]-2,3-dihydro-3-ethyl-4-methylthiazole carboxylate,
5-methyl-3-(1-methylethyl)-4-phenyl-2(3 H )-thiazolone-(1-methylethylidene)-hydrazone, 4,5-dimethyl-3-(1-methylethyl)-2(3H)-thiazolone-(1-methylethylidene) hydrazone,
3-(1-methylethyl)-4,5-diphenyl-2(3H)-thiazolone-(1-methylethylidene)hydrazone,
4-methyl-3-propyl-2(3H)-thiazolone-(1-methylethylidene)hydrazone,
4,5-dimethyl-3-propyl-2(3H)-thiazolone-(1-methylethylidene)hydrazone,
4,5-diphenyl-3-propyl-2(3H)-thiazolone-(1-methylethylidene)hyd razone,
3-butyl-4,5-dimethyl-2(3H)-thiazolone-(1-methylethylidene)hydrazone,
3-butyl-4,5-diphenyl-2(3H)-thiazolone-(1-methylethylidene)hydrazone,
4,5-dimethyl-3-(2-methylpropyl)-2(3H)-thiazolone-(1-methylethylidene)hydrazone,
3-(2-methylpropyl)-4,5-diphenyl-2(3H)-thiazolone-(1-methylethylidene)hydrazone,
3-allyl-2(3H)-thiazolone-(1-methylethylidene)hydrazone,
3-allyl-4-methyl-2(3H)-thiazolone-(1-methylethylidene)hydrazone,
3-allyl-4-tert-butyl-2(3H)-thiazolone-(1-methylethylidene)hydrazone,
3-allyl-4-phenyl-2(3H)-thiazolone-(1-methylethylidene)hydrazone,
3-aIIyi-4,5-dimethyl-2(3H)-thiazolone-(1-methylethylidene)hydrazone,
3-allyl-4,5-diphenyl-2(3H)-thiazolone-(1-methylethylidene)hydrazone,
3-hydroxyethyl-2(3H)-thiazolone-(1-methylethylidene)hydrazone,
3-hydroxyethyl-4-methyl-2(3H )-thiazolone-(1-methylethylidene)hyd razone,
3-hydroxyethyl-4,5-dimethyl-2(3H)-thiazolone-(1-methylethylidene)hyd razone,
3-aminoethyl-2(3H)-thiazolone-(1-methylethylidene)hydrazone,
3-aminoethyl-4-methyl-2(3H)-thiazolone-(1-methylethylidene)hydrazone,
3-aminoethyl-4,5-dimethyl-2(3H)-thiazolone-(1-methylethylidene)hydrazone,
3-phenyl-2(3H)-thiazolone-(1-methylethylidene)hydrazone,
3,4-diphenyl-2(3H)-thiazolone-(1-methylethylidene)hydrazone,
4-methyl-3-phenyl-2(3H)-thiazolone-(1-methylethylidene)hydrazone,
4-p-biphenylyl-3-phenyl-2(3H)-thiazolone-(1-methylethylidene)hyd razone,
4-(4-methoxy)phenyl-3-phenyl-2(3H)-thiazolone-(I -methylethylidene)hyd razone,
4-tert.butyl-3-phenyl-2(3H)-thiazolone-(1-methylethylidene)hydrazone,
4,5-dimethyl-3-phenyl-2(3H)-thiazolone-(1-methylethylidene)hydrazone,
5-methyl-3,4-diphenyl-2(3H)-thiazolone-(1-methylethylidene)hydrazone,
3,4,5-triphenyl-2(3H)-thiazolone-(1-methylethylidene) hydrazone,
4,5-dimethyl-3-(phenylmethyl)-2(3H)-thiazolone-(1-methylethylidene)hydrazone,
4-phenyl-3-(phenylmethyl)-2(3H)-thiazolone-(1-methylethylidene)hydrazone,
5-methyl-4-phenyl-3-(phenyl methyl)-2(3 H )-thiazolone-(1-methylethylidene)-hydrazone,
3-methyl-4,5,6,7-tetrahydro-2(3H )-benzothiazole-(1-methylethylidene)hyd razone,
3-methyl-2(3H)-benzothiazole-(1-methylethylidene)hydrazone,
3,6-dimethyl-2(3H )-benzothiazole-(1-methylethylidene) hydrazone,
6-chloro-3-methyl-2(3H)-benzothiazole-(1-methylethylidene)hydrazone,
7-chloro-3-methyl-2(3H)-benzothiazole-(1-methylethylidene)hydrazone,
6-hydroxy-3-methyl-2(3H)-benzothiazole-(1-methylethylidene)hydrazone,
5-methoxy-3-methyl-2(3H)-benzothiazole-(1-methylethylidene)hydrazone,
7-methoxy-3-methyl-2(3H)-benzothiazole-(1-methylethylidene)hydrazone,
5,6-dimethoxy-3-methyl-2(3H)-benzothiazole-(1-methylethylidene)hydrazone,
5-ethoxy-3-methyl-2(3H)-benzothiazole-(1-methylethylidene)hydrazone,
6-ethoxy-3-methyl-2(3H)-benzothiazole-(1-methylethylidene)hydrazone,
3-methyl-5-nitro-2(3H)-benzothiazole-(1-methylethylidene)hydrazone, 3-methyl-6-nitro-2(3H)-benzothiazole-(1-methylethylidene)hydrazone,
5-acetamido-3-methyl-2(3H)-benzothiazole-(1-methylethylidene)hydrazone,
6-acetamido-3-methyl-2(3H)-benzothiazole-(1-methylethylidene)hydrazone,
5-anilino-3-methyl-2(3H)-benzothiazole-(1-methylethylidene)hydrazone,
6-anilino-3-methyl-2(3H)-benzothiazole-(1-methylethylidene)hydrazone,
2-[(1-methylethylidene)hydrazono]-2,3-dihydro-3-methyl-6-benzothiazole carboxylic acid,
2-[(1-methylethylidene)hydrazono]-2,3-dihydro-3-methyl-4-benzothiazole sulfonic acid,
2-[(1-methylethylidene)hydrazono]-2,3-dihydro-3-methyl-5-benzothiazole sulfonic acid,
2-[(1-methylethylidene)hydrazono]-2,3-dihydro-3-methyl-6-benzothiazole sulfonic acid,
2-[(1-methylethylidene)hydrazono]-2,3-dihydro-3-methyl-7-benzothiazole sulfonic acid,
2-[(1-methylethylidene)hydrazono]-2,3-dihydro-N,N-3-trimethyl-6-benzothiazole sulfonamide [(2-[(1-methylethylidene)hydrazono]-2,3-dihydro-3-methyl-6-benzothiazole)oxy]acetic hydrazide,
3-ethyl-2(3H)-benzothiazole-(1-methylethylidene)hydrazone,
6-ethoxy-3-ethyl-2(3H)-benzothiazole-(1-methylethylidene)hydrazone,
3-propyl-2(3H)-benzothiazole-(1-methylethylidene)hydrazone,
3-butyl-2(3H)-benzothiazole-(1-methylethylidene)hydrazone and
3-hexyl-2(3H)-benzothiazole-(1-methylethylidene)hydrazone.

4. The agent as defined in claim 1, in which said at least one coupler is selected from the group consisting of N-(3-dimethylaminophenyl)urea, 2,6-diamino-pyridine, 2-amino-4-[(2-hydroxyethyl)-amino]-anisole, 2,4-diamino-1-fluoro-5-methyl-benzene, 2,4-diamino-1-methoxy-5-methylbenzene, 2,4-diamino-1-ethoxy-5-methyl-benzene, 2,4-diamino-1-(2-hydroxyethoxy)-5-methyl benzene, 2,4-di[(2-hydroxy-ethyl)amino]-1,5-dimethoxy-benzene, 2,3-diamino-6-methoxypyridine, 3-amino-6-methoxy-2-(methylamino)-pyridine, 2,6-diamino-3,5-dimethoxypyridine, 3,5-diamino-2,6-dimethoxypyridine, 1,3-diaminobenzene, 2,4-diamino-1-(2-hydroxy-ethoxy)-benzene, 1,3-diamino-4-(2,3-dihydroxypropoxy)benzene, 1,3-diamino-4-(3-hydroxypropoxy)-benzene, 1,3-diamino-4-(2-methoxyethoxy)-benzene, 2,4-diamino-1,5-di(2-hydroxyethoxy)-benzene, 1-(2-aminoethoxy)-2,4-diamino-benzene, 2-amino-1-(2-hydroxyethoxy)-4-methylaminobenzene, 2,4-diamino-phenoxyacetic acid, 3-[di(2-hydroxyethyl)amino]-aniline, 4-amino-2-di[(2-hydroxy-ethyl)amino]-1-ethoxybenzene, 5-methyl-2-(1-methyl-ethyl)phenol, 3-[(2-hydroxy-ethyl)amino]aniline, 3-[(2-aminoethyl)amino] aniline, 1,3-di(2,4-diaminophenoxy)-propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methyl phenol, 3-amino-2,4-dichlorophenol, 5-amino-2,4-dichlorophenyl, 3-amino-2-methylphenol, 3-amino-2-chloro-6-methylphenol, 3-aminophenol, 2-[(3-hydroxy-phenyl)amino]-acetamide, 5-[(2-hydroxyethyl)amino]-4-methoxy-2-methylphenol, 5-[(2-hydroxyethyl)amino]-2-methylphenol, 3-[(2-hydroxyethyl)amino]-phenol, 3-[(2-methoxyethyl)amino]-phenol, 5-amino-2-ethyl phenol, 5-amino-2-methoxy-phenol, 2-(4-amino-2-hydroxy-phenoxy)ethanol, 5-[(3-hydroxypropyl)amino]-2-methylphenol, 3-[(2,3-dihydroxy-propyl)amino]-2-methylphenol, 3-[(2-hydroxyethyl)-amino]-2-methylphenol, 2-amino-3-hydroxypyridine, 2,6-dihydroxy-3,4-dimethyl-pyridine, 5-amino-4-chloro-2-methyl-phenol, 1-naphthol, 2-methyl-1-naphthol, 1,5-dihydroxynaphthalene, 1,7-dihydroxy-naphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxy-benzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedoxyaniline, 5-[(2-hydroxyethyl )amino]-1,3-benzodioxole, 6-bromo-1-hydroxy-3,4-methylene-dioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazoline, 5,6-dihydroxyindole, 5,6-dihydroxyindole, 5-hydroxyindole, 6-hydroxyindole, 7-hydroxyindole and 2,3-indolinedione.

5. The agent as defined in claim 1, in which said persulfate salt is selected from the group consisting of potassium persulfate, sodium persulfate and ammonium persulfate.

6. The agent as defined in claim 1, containing said at least one hydrazone derivative of the formula (I), said at least one coupler and said persulfate salt in a total amount from 0.01 to 10 weight percent.

7. The agent as defined in claim 1, containing from 0.01 to 10 weight percent of at least one physiologically harmless direct dye, and in which said at least one physiologically harmless direct dye is selected from the group consisting of cationic dyes, anionic dyes, disperse dyes, nitro dyes, azo dyes, quinone dyes and triphenylmethane dyes.

8. The agent as defined in claim 1, having a pH from 6 to 10.

9. The agent as defined in claim 1, consisting of a hair colorant.

10. A two-component kit, consisting of a dye carrier composition (A1) and another dye carrier composition (A2),
in which said dye carrier composition (A1) contains at least one hydrazone derivative of formula (I), or a physiologically compatible salt thereof:

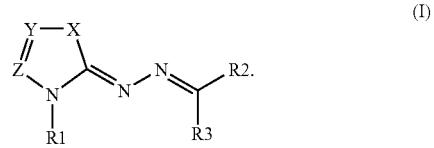

(I)

in which X denotes oxygen, sulfur, or N—R4;
Y denotes C—R5 or nitrogen, and
Z denotes C—R6 or nitrogen;
provided that a heterocyclic part of the derivative of the formula (I) contains at the most three heteroatoms;
in which R1 and R4 are equal or different and, independently of each other, each denote a saturated or unsaturated $(C_1\text{-}C_{12})$-alkyl group, a $(C_1\text{-}C_{12})$-alkyl group substituted with a halogen atom, a hydroxy-$(C_1\text{-}C_{12})$-alkyl group, an amino-$(C_1\text{-}C_{12})$-alkyl group, a $(C_1\text{-}C_{12})$-alkylsulfonic acid group, a formyl group, a C(O)—$(C_1\text{-}C_{12})$-alkyl group, a C(O)-phenyl group, a C(O)NH—(C$_1$-C$_{12}$)-alkyl group, a C(O)NH-phenyl group, a substituted or unsubstituted phenyl group, or a benzyl group;

R2 and R3 are equal or different and, independently of each other, each denote a saturated or unsaturated (C$_1$-C$_{12}$)-alkyl group;

R5 and R6 are equal or different and, independently of each other, each denote hydrogen, a halogen atom, a saturated or unsaturated (C$_1$-C$_{12}$)-alkyl group, a (C$_1$-C$_{12}$)-alkyl group substituted with a halogen atom, a (C$_1$-C$_{12}$)-hydroxyalkyl group, a (C$_1$-C$_{12}$)-alkoxy group, a cyano group, a nitro group, an amino group, a (C$_1$-C$_{12}$)-alkylamino group, a (C$_1$-C$_{12}$)-dialkylamino group, a carboxylic acid group, a C(O)O—(C$_1$-C$_{12}$)-alkyl group, a substituted or unsubstituted C(O)O-phenyl group, a substituted or unsubstituted phenyl group, or a naphthyl group;

and with the proviso that, if Y and Z denote C—R3 and C—R4, then R5 and R6 together with a remainder of the formula (I) form a heterocyclic or carbocyclic, saturated or unsaturated, substituted or unsubstituted ring system; and in which said another dye carrier composition (A2) contains at least one coupler, a persulfate salt, and optionally a pH-adjusting agent.

11. A two-component kit comprising a first component and a second component, in which said first component consists of a powder containing at least one coupler, at least one hydrazone derivative of formula I, a persulfate salt, and optionally at least one powdered cosmetic additive, provided that the at least one hydrazone derivative of the formula (I), the at least one coupler and the persulfate salt are in solid form,

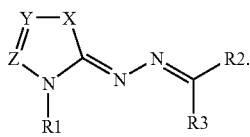

(I)

in which X denotes oxygen, sulfur, or N—R4;
Y denotes C—R5 or nitrogen, and
Z denotes C—R6 or nitrogen;

provided that a heterocyclic part of the derivative of the formula (I) contains at the most three heteroatoms;

in which R1 and R4 are equal or different and, independently of each other, each denote a saturated or unsaturated (C$_1$C$_{12}$)-alkyl group, a (C$_1$-C$_{12}$)-alkyl group substituted with a halogen atom, a hydroxy-(C$_1$-C$_{12}$)-alkyl group, an amino-(C$_1$-C$_{12}$)-alkyl group, a (C$_1$-C$_{12}$)-alkylsulfonic acid group, a formyl group, a C(O)—(C$_1$-C$_{12}$)-alkyl group, a C(O)-phenyl group, a C(O)NH—(C$_1$-C$_{12}$)-alkyl group, a C(O)NH-phenyl group, a substituted or unsubstituted phenyl group, or a benzyl group;

R2 and R3 are equal or different and, independently of each other, each denote a saturated or unsaturated (C$_1$-C$_{12}$)-alkyl group;

R5 and R6 are equal or different and, independently of each other, each denote hydrogen, a halogen atom, a saturated or unsaturated (C$_1$-C$_{12}$)-alkyl group, a (C$_1$-C$_{12}$)-alkyl group substituted with a halogen atom, a (C$_1$-C$_{12}$)-hydroxyalkyl group, a (C$_1$-C$_{12}$)-alkoxy group, a cyano group, a nitro group, an amino group, a (C$_1$-C$_{12}$)-alkylamino group, a (C$_1$-C$_{12}$)-dialkylamino group, a carboxylic acid group, a C(O)O—(C$_1$-C$_{12}$)-alkyl group, a substituted or unsubstituted C(O)O-phenyl group, a substituted or unsubstituted phenyl group, or a naphthyl group;

and with the proviso that, if Y and Z denote C—R3 and C—R4, then R5 and R6 together with a remainder of the formula (I) form a heterocyclic or carbocyclic, saturated or unsaturated, substituted or unsubstituted ring system; and in which said second component consists of water or a liquid cosmetic preparation optionally containing a pH-adjusting agent.

12. A method of coloring hair, said method comprising the steps of:

a) providing a colorant of the hair, said colorant containing a persulfate salt as oxidant; at least one coupler, or a physiologically compatible salt thereof; and at least one hydrazone derivative of formula (I), or a physiologically compatible salt thereof:

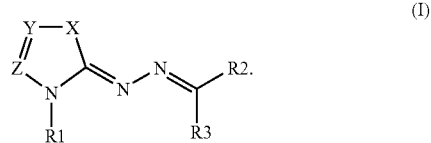

(I)

in which X denotes oxygen, sulfur, or N—R4;
Y denotes C—R5 or nitrogen, and
Z denotes C—R6 or nitrogen;

provided that a heterocyclic part of the derivative of the formula (I) contains at the most three heteroatoms;

in which R1 and R4 are equal or different and, independently of each other, each denote a saturated or unsaturated (C$_1$ C$_{12}$)-alkyl group, a (C$_1$-C$_{12}$)-alkyl group substituted with a halogen atom, a hydroxy-(C$_1$-C$_{12}$)-alkyl group, an amino-(C$_1$-C$_{12}$)-alkyl group, a (C$_1$-C$_{12}$)-alkylsulfonic acid group, a formyl group, a C(O)—(C$_1$-C$_{12}$)-alkyl group, a C(O)-phenyl group, a C(O)NH—(C$_1$-C$_{12}$)-alkyl group, a C(O)NH-phenyl group, a substituted or unsubstituted phenyl group, or a benzyl group;

R2 and R3 are equal or different and, independently of each other, each denote a saturated or unsaturated (C$_1$-C$_{12}$)-alkyl group;

R5 and R6 are equal or different and, independently of each other, each denote hydrogen, a halogen atom, a saturated or unsaturated (C$_1$-C$_{12}$)-alkyl group, a (C$_1$-C$_{12}$)-alkyl group substituted with a halogen atom, a (C$_1$-C$_{12}$)-hydroxylalkyl group, a (C$_1$-C$_{12}$)-alkoxy group, a cyano group, a nitro group, an amino group, a (C$_1$-C$_{12}$)-alkylamino group, a (C$_1$-C$_{12}$)-dialkylamino group, a carboxylic acid group, a C(O)O-(C$_1$-C$_{12}$)-alkyl group, a substituted or unsubstituted C(O)O-phenyl group, a substituted or unsubstituted phenyl group, or a naphthyl group;

and with the proviso that, if Y and Z denote C—R3 and C—R4, then R5 and R6 together with a remainder of the formula (I) form a heterocyclic or carbocyclic, saturated or unsaturated, substituted or unsubstituted ring system;

b) applying said colorant to the hair;

c) allowing said colorant to remain on the hair for an exposure time of 5 to 60 minutes at a temperature from 20 to 50° C. after the applying; and then d) rinsing the hair with water, optionally washing the hair with a shampoo and then drying the hair.

13. A method of coloring hair, said method comprising the steps of:

a) providing a two-component kit for coloring the hair, said two-component kit consisting of a dye carrier composition (A1) and another dye carrier composition (A2), in which said dye carrier composition (A1) contains at least one hydrazone derivative of formula (I), or a physiologically compatible salt thereof:

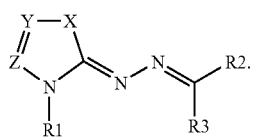

(I)

in which X denotes oxygen, sulfur, or N—R4;
Y denotes C—R5 or nitrogen, and
Z denotes C—R6 or nitrogen;
provided that a heterocyclic part of the derivative of the formula (I) contains at the most three heteroatoms;
in which R1 and R4 are equal or different and, independently of each other, each denote a saturated or unsaturated $(C_1-C_{12})$-alkyl group, a $(C_1-C_{12})$-alkyl group substituted with a halogen atom, a hydroxy-$(C_1-C_{12})$-alkyl group, an amino-$(C_1-C_{12})$-alkyl group, a $(C_1-C_{12})$-alkylsulfonic acid group, a formyl group, a C(O)—$(C_1-C_{12})$-alkyl group, a C(O)-phenyl group, a C(O)NH—$(C_1-C_{12})$-alkyl group, a C(O)NH-phenyl group, a substituted or unsubstituted phenyl group, or a benzyl group;

R2 and R3 are equal or different and, independently of each other, each denote a saturated or unsaturated $(C_1-C_{12})$-alkyl group;

R5 and R6 are equal or different and, independently of each other, each denote hydrogen, a halogen atom, a saturated or unsaturated $(C_1-C_{12})$-alkyl group, a $(C_1-C_{12})$-alkyl group substituted with a halogen atom, a $(C_1-C_{12})$-hydroxyalkyl group, a $(C_1-C_{12})$-alkoxy group, a cyano group, a nitro group, an amino group, a $(C_1-C_{12})$-alkylamino group, a $(C_1-C_{12})$-dialkylamino group, a carboxylic acid group, a $C(O)O$-$(C_1-C_{12})$-alkyl group, a substituted or unsubstituted C(O)O-phenyl group, a substituted or unsubstituted phenyl group, or a naphthyl group;

and with the proviso that, if Y and Z denote C—R3 and C—R4, then R5 and R6 together with a remainder of the formula (I) form a heterocyclic or carbocyclic, saturated or unsaturated, substituted or unsubstituted ring system; and in which said another dye carrier composition (A2) contains at least one coupler, a persulfate salt, and optionally a pH-adjusting agent;

b) immediately prior to application to the hair, preparing a ready-to-apply colorant mixture (A) by mixing said another dye carrier composition (A2) with said dye carrier composition (A1) and optionally with an alkalinizing agent or an acid; and then c) applying said ready-to-apply colorant mixture (A) to the hair;

d) after the applying of step c), allowing the ready-to-apply colorant mixture (A) to remain on the hair for an exposure time of 5 to 60 minutes at a temperature from 20 to 50° C.; and then e) rinsing the hair with water, optionally washing the hair with a shampoo and then drying the hair.

* * * * *